United States Patent
Griffith (10) Patent No.: US 9,551,686 B1
(45) Date of Patent: Jan. 24, 2017

(54) APPARATUS AND METHOD OF NON-INVASIVE ANALYSIS AND IDENTIFICATION OF PHYSICAL MATERIALS IN REAL TIME

(71) Applicant: William F. Griffith, Decatur, TX (US)

(72) Inventor: William F. Griffith, Decatur, TX (US)

(*) Notice: Subject to any disclaimer, the term of this patent is extended or adjusted under 35 U.S.C. 154(b) by 0 days.

(21) Appl. No.: 14/203,450

(22) Filed: Mar. 10, 2014

Related U.S. Application Data (60) Provisional application No. 61/775,546, filed on Mar. 9, 2013.

(51) Int. Cl.
*G01N 27/72* (2006.01)
*G01N 22/00* (2006.01)
*G01R 33/12* (2006.01)

(52) U.S. Cl.
CPC ............ *G01N 27/72* (2013.01); *G01N 22/00* (2013.01); *G01R 33/12* (2013.01)

(58) Field of Classification Search
CPC ...... G01N 27/9046; G01N 27/00; G01R 33/12
USPC ................................................ 324/227–243
See application file for complete search history.

(56) References Cited

U.S. PATENT DOCUMENTS

| | | | | |
|---|---|---|---|---|
| 3,249,882 A | * | 5/1966 | Stern | ............... H03F 7/02 330/4.6 |
| 3,691,453 A | * | 9/1972 | Rupp, Jr. | ............... G01R 33/60 324/316 |
| 2013/0093424 A1 | * | 4/2013 | Blank | ............... G01R 33/60 324/316 |
| 2015/0028211 A1 | * | 1/2015 | Nakamura et al. | ...... 250/339.06 |

* cited by examiner

*Primary Examiner* — Jay Patidar
(74) *Attorney, Agent, or Firm* — Guy V. Manning (57) ABSTRACT

A method and apparatus for non-invasive, real time analysis of physical and chemical properties of a medium employs electromagnetic waves induced by an excitation transducer within longitudinally magnetized strips of ferromagnetic film serving as a waveguide. A physical medium juxtaposed to the wave guide induces a charge center encountered by the pulsed electromagnetic waves. The characteristics of changes induced by the physical medium within the pulsed electromagnetic wave, such as permittivity and permeability effects, boundary oscillations and phase changes are read by detection transducers and transmitted to software for analysis of the characteristics of the physical medium.

15 Claims, 6 Drawing Sheets

APPARATUS AND METHOD OF NON-INVASIVE ANALYSIS AND IDENTIFICATION OF PHYSICAL MATERIALS IN REAL TIME

This application claims priority from Provisional Application Ser. No. 61/775,546, filed Mar. 9, 2013.

BACKGROUND OF THE INVENTION

1. Field of the Invention

This invention relates generally to profiling physical and chemical media utilizing electromagnetic waves. More particularly, this invention relates to an instrument and method for analyzing materials in the proximity of soliton waves propagating through a wave guide and detecting effects on the soliton waves induced by the materials.

2. Description of Related Art

Periodic oscillations of energy, commonly referred to as electromagnetic waves, have been used to analyze chemical or physical properties of materials for many years. Beginning with the early exploration of light in the 1600's by Isaac Newton, Robert Hooke, and others, the application of electromagnetic waves to analyze chemical or physical properties of media now spans many areas of analytical chemistry including atomic absorption spectroscopy (AA), infrared absorption spectroscopy (IR), and microwave absorption (MW).

A stable form of electromagnetic energy producing a selected wavelength within a sampling device and a detector may be used to produce a measurable output signal. From the output signals, emission, absorption and fluorescence spectra of materials, and data from liquid and gas samples may be collected and analyzed. Depending on the wavelength, or energy, of the electromagnetic wave used, molecular and atomic data can be obtained.

Generally, spectroscopic methods are based on energy absorption, emission or fluorescence. A molecule can undergo a transition from a high energy state to a low energy state and emit energy as a photon, or reverse the process through the absorption of energy. Absorption and emission can occur at the electronic, vibrational, or rotational levels where elementary excitations may be found. Excitations can be described as ordinary sinusoidal waves representing periodic physical properties. Sinusoidal waves typically exhibit a dispersive response to the material in which the sinusoidal waves travel as well as exhibit a loss of energy in motion. Dispersion and loss of energy in the sinusoidal wave can present analytical limitations within a material, especially in a multi-phase medium.

High energy electromagnetic waves such as X-ray, ultraviolet, and infrared waves have been used to explore the dynamic environment of charge motion, potential inclusive lattice differentiation, boundaries, and variable quantum states found in many materials. However, as the transverse, oscillating electric field and accompanying magnetic field of an electromagnetic wave passes through a material, each field can be stressed or strained such that dislocations, dipoles, changes in permittivity and permeability, boundary oscillation frequencies, and other physical characteristics of the material can complicate the transmission of the high energy wave through the material. As a result, electromagnetic waves, particularly high energy waves, such as microwaves have not proved useful for exploring the charge motion, potential inclusive lattice differentiation, boundaries and variable quantum states, because the low frequency, long wave length, and potential peak broadening of high energy waves restricts possible applications.

Electromagnetic characteristics are present or can be created within most materials, and most materials create an environment of varied electromagnetic forces, varied charge centers and ionic crystal lattices. An incident wave originating outside a material can be influenced by moving charges or electromagnetic fields within or near the material, thus creating a characteristic interaction signature that can be seen within both incident and reflected waves. Further, significant penetration of the material and increased analytical depth may be achieved.

A crystalline, medium/liquid interface, or an amorphous material may have dislocations which could create a detectable field anomaly. Dislocation is defined as any change within surface or subsurface morphology including polarity and other charge characteristics. A change in surface profile, cracks or breaking within the material, boundaries within the material, an inclusion of another type of atom or structure within an overall crystal structure, and displacement of atomic groups within the structure of the material, are all to be considered dislocations. Field anomalies created by such dislocations result in changes within internal electrical or magnetic field vectors.

A method and device that takes advantage of these principles, without the disabilities of high energy electromagnetic waves, for identifying a material by the environment of varied electromagnetic forces of the material, would be highly useful. A method and device that can monitor material properties externally, without invasive techniques, would be valuable in a variety of industries, such as process stream manufacturing, biomedical and pharmaceutical.

SUMMARY OF THE INVENTION

In a particular embodiment, the formation of electromagnetic waves is used as a method of profiling physical and chemical properties of multiphase media. The electromagnetic waves are induced within longitudinally magnetized strips of conductive film using a waveguide. In a particular embodiment, electromagnetic waves demonstrating soliton characteristics are particularly useful within the process.

A soliton wave is a non-destructive self-reinforcing solitary wave packet pulse that maintains shape while it travels at constant speed. Soliton waves are caused by a cancellation of nonlinear and dispersive effects in a medium. The term "dispersive effects" refers to a property of certain systems where the speed of the wave varies according to frequency. Because of the varied electromagnetic forces found in most material, the impact of the varied electromagnetic forces on incident waves, such as microwave soliton waves, results in a change within the character of the electromagnetic wave. Analysis of wave characteristics of the electromagnetic wave, which includes permittivity and permeability effects and boundary oscillations and phase changes allows for analytical applications.

In a particular embodiment, microwave induced electromagnetic waves demonstrating sinusoidal and soliton characteristics propagate on the surface of a thin-film, non-linear ferromagnetic waveguide through a multi-phase test medium, and are detected and analyzed after passing through the test material. Signal enhancement may occur within the waveguide by phase coherent recovery signals. In a particular embodiment, the ferromagnetic waveguide is a monocrystalline YIG (yttrium iron garnet) film. Magnetostatic spin waves (MSW), including those having non-linear soliton characteristics, are produced within the YIG thin waveguide and spin waves employed to analytically scan any solid, liquid or gas phase medium, within either a static or variable magnetic field.

During use of at least one of the disclosed embodiments, a sample medium is positioned near the surface of a film that receives either a continuous or pulsed electromagnetic wave input signal. An output signal is collected from the film and the output characteristics of the electromagnetic wave are contrasted to the input wave signal to determine the electrical and magnetic properties of the sample medium. The measured output characteristics are used to determine general sample medium properties such as concentration or more specific characteristics such as medium dipole centers, interactions, hydrogen bonding clusters, and magnetic resonance.

One particular advantage provided by at least one of the disclosed embodiments is that the profiling of the medium could be used within manufacturing processes in which product composition must be monitored continuously, such as within petroleum processing and solvent manufacturing.

Another particular advantage provided by at least one of the disclosed embodiments is that biological or medical processes can be externally measured or monitored in real time, thus reducing the need for more invasive analytical methods. For example, biological media such as patient physiology may be monitored externally. Modulation and phase resonance recovery of wave guide surface wave and applied magnetic field also allows magnetic resonance imaging and material profiling.

BRIEF DESCRIPTION OF THE DRAWINGS

The novel features believed characteristic of the present invention are set forth in appended claims. The invention itself, however, as well as a preferred mode of use and further objects and advantages thereof, will best be understood by reference to the following detailed description of an illustrative embodiment when read in conjunction with the accompanying drawings, wherein:

DETAILED DESCRIPTION OF A PREFERRED EMBODIMENT

Figure 1:
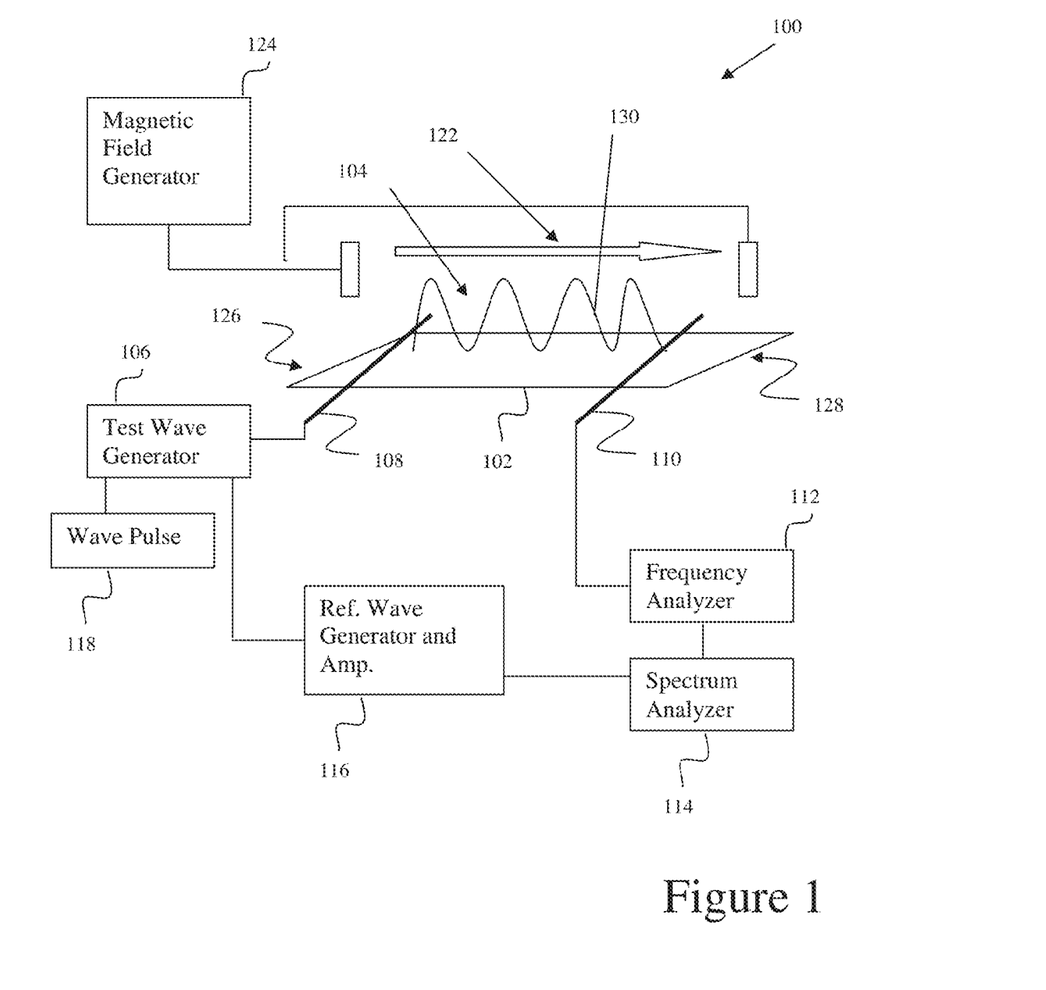
FIG. 1 is a block diagram of general instrumentation configuration showing a general profiling assembly in which the illustrative embodiments may be implemented.

Referring to the figures, and particularly now to FIGS. 1-3B, illustrative embodiments of the present invention include an electromagnetic pulse transmission probe useful for profiling of charge centers in a medium. In FIG. 1, electromagnetic wave sensor 100 contains waveguide film 102, sampling area 104, waveguide generator 106, excitation transducer 108, detection transducer 110, frequency analyzer 112, spectrum analyzer 114, reference wave generator and amplifier 116, wave pulse source 118, and magnetic field 122. Electromagnetic wave 130 generated by waveguide generator 106 may be modified to obtain specific electrical or magnetic characteristics required during an application. Wave 130 is sent to excitation transducer 108 and reference wave generator and amplifier 116, for contrasting with the resulting wave 130 as it is detected by transducer 110.

Waveguide film 102 is a physical, conductive structure that guides or allows wave 130 generated by electromagnetic wave generator 106 to traverse across a sample medium (see FIG. 2A) positioned within sampling area 104. In a particular embodiment, waveguide film 102 is prepared using liquid phase epitaxi or other known manufacturing processes. In a particular embodiment, waveguide film 102 is a YIG crystal, YAG crystal, YIBG crystal, or some other similar type of crystal.

In a particular embodiment, waveguide 102 is a rectangular waveguide. The nature of waveguide 102 can be modified structurally or chemically to address specific electromagnetic wave propagation properties of the medium to be analyzed. In a particular embodiment, waveguide 102 is a yttrium iron garnet (YIG) waveguide, a yttrium-aluminum garnet (YAG) waveguide, a yttrium iron boron garnet (YIBG) waveguide, or some other similar waveguide.

Sampling area 104 is the area or environment proximate to waveguide film 102 between excitation transducer 108 and detection transducer 110. In a particular embodiment, sampling area 104 is between about 0.0 millimeters (mm) (in contact with waveguide film 102) to about 1.0 centimeter (cm) from waveguide film 102. However, the distance from sampling area 104 to waveguide film 102 depends on various properties of electromagnetic wave sensor 100 including, but not limited to, the strength and frequency of waveguide 130 and the sensitivity of the equipment being used in electromagnetic wave sensor 100.

Magnetic field 122 is created by magnetic field generator 124 and is in contact with at least a portion of sampling area 104. Magnetic field 122 helps to propagate wave 130 across waveguide film 102. Magnetic field 122 may be a static magnetic field produced by an electromagnetic or permanent magnet such as a neodymium magnet or other rare earth magnet. In a particular embodiment, magnetic field 122 is modulated.

Excitation transducer 108 is located on input end 126 of waveguide film 102 and delivers wave 130 generated by waveguide generator 106 to waveguide film 102 to create magnetostatic spin wave signals. In a particular embodiment, excitation transducer 108 is a ferromagnetic tip surface contact. Detection transducer 110 is located on output end 128 of waveguide film 102. Detection transducer 110 detects magnetostatic spin wave signals after they have passed through sampling area 104 and transfers them to frequency analyzer 112.

Frequency analyzer 112 analyzes the frequency of detected magnetostatic spin wave signal 130 as it emerges from transducer 110. A suitable frequency analyzer 112 is available as Hewlett Packard model 541T frequency analyzer with 8555A r.f and 8552B i.f sections, commercially available from Hewlett-Packard Co. of in Palo Alto, Calif.

Frequency analyzer 112 sends a signal to spectrum analyzer 114. In a particular embodiment, spectrum analyzer 114 is located on a personal computer that contains spectrum analyzing software. A suitable spectrum analyzing software is SigView 2.0.0 program commercially available from SignalLab located in Pforzheim, Germany. In addition, spectrum analyzer 114 receives a reference signal from reference wave generator and amplifier 116. Reference wave generator and amplifier 116 provides a reference signal for spectrum analyzer 114 to compare to the signal received from frequency analyzer 112. In a particular embodiment, the reference signal is the received wave 130 generated by waveguide generator 106.

During use of electromagnetic wave sensor 100, wave 130 demonstrates an induced spin-wave character, including a soliton wave pattern, derived from a selected microwave pulse input. The induced spin-wave character is impacted by applied additional wave sources and reflected wave patterns from the medium in the sample area 104. The final wave pattern detected by detection transducer 110 is also impacted upon by the overall electrical and magnetic vector product of the medium in sample area 104 as wave 130 passes down waveguide 102 near the sample. The length of waveguide 102 and sample area 104 depends on various properties of the electromagnetic wave sensor 100 including, but not limited to, the strength and frequency of wave 130 and the sensitivity of the equipment being used in sensor 100.

Referring now specifically to FIGS. 2A-2D, an illustrative embodiment of profiling mounting assembly 200 is illustrated. Profile mounting assembly 200 contains YIG film 202, sampling area 204, excitation transducer 208, and detection transducer 210. YIG film 202 has input end 220 and output end 222. Assembly 200 preferably is mounted on a stable, planar substrate 218 such as a section of pre-drilled molded thermoplastic circuit board backing, commercially available as catalog No. 276-170 from RadioShack Corporation of Fort Worth, Tex. YIG film 202 is similar in structure and function to waveguide film 102 of FIG. 1. Sampling area 204 is similar in structure and function to sampling area 104, shown in FIG. 1. Excitation transducer 208 is similar in structure and function as excitation transducer 108, shown in FIG. 1. Detection transducer 210 is similar in structure and function to detection transducer 110, shown in FIG. 1.

In a particular embodiment, YIG film 202 comprises a thin film waveguide, preferably having a thickness between 5.0-7.2 microns (micrometers), and more preferably toward the lower end of that range. In a particular embodiment, YIG film 202 preferably is between 1.0 millimeters (mm) and 1.5 mm in width to reduce transverse instabilities and diffraction effects within soliton wave 130. In combination, these parameters substantially limit propatation of soliton wave 130 to a path parallel to the longitudinal axis between input end 220 and output end 222 of YIG waveguide 202. Because only waves 130 traveling in a forward direction between input end 220 and output end 222, YIG film 202 preferably is tapered at output end 222 to limit pulse reflection.

In a particular embodiment, YIG film 202 preferably is between approximately 20 mm and 30 mm in length, and more preferably about 22.4 mm in length. This allows a realistic space for sampling area 104. In another particular embodiment, YIG film 202 preferably is about 22.4 mm in length. In one particular embodiment, the distance between excitation transducer 208 and detection transducer 210 generally defines sample area 204.

In a particular embodiment, YIG film 202 comprises a combination of one or more, or all, of the foregoing dimensional parameters. One having ordinary skill in the art will recognize, however, that the thickness, length and width of YIG film 202 depends on various properties of profile mounting assembly 200 including, but not limited to, the strength and frequency of waveguide 102 and the sensitivity of the equipment being used in the profile mounting assembly 200.

Sample area 204 preferably is between about 10 mm and about 20 mm in length. One having ordinary skill in the art will recognize, however, that the length of sample area 204 depends on various properties of the profile mounting assembly 200 including, but not limited to, the strength and frequency of a waveguide and the sensitivity of the equipment being used in the profile mounting assembly 200. In a particular embodiment, the sample area 204 is about 14.4 mm in length.

An electromagnetic wave with an amplitude of 1.5. 2.0 mm, would be consistent with the production of non-linear soliton waves 130. Soliton waves above that amplitude could suffer from environmental noise problems, even with shielding. Accordingly, in a particular embodiment, samples 216 placed in sample area 204 preferably are positioned within 1.5 mm of the surface of YIG film 202. A suitable sample vessel 214 (FIGS. 2A, 2B) is a standard optical glass laboratory cuvette, commercially available, having a bottom thickness of approximately 1 mm, placing a test sample within the cuvette well within the preferred range of distance from YIG film 202.

In a particular embodiment, excitation transducer 208 and detection transducer 210 couple to YIG film 202 by simple copper strips. In another particular embodiment, the copper strips are replaced by spring-loaded contact probes 212 commercially available. In another particular embodiment, contact probes 212 are similar in nature to magnetic tip compute hard drive probes, also commercially available. One having ordinary skill in the art will recognize that all such contact means are considered within the spirit and scope of the present invention.

In a particular embodiment, wave generator 106 may be a klystron microwave generator. In an alternate embodiment, wave generator may be a microwave sweep oscillator. In a particular embodiment of microwave sweep oscillator, wave generator 106 operates with a sweep range of 3.8-4.1 gigahertz (gHz) with a bandwidth of 30 kilohertz (kHz), 10 per division scan width and input attenuation of 0 dB.

Figure 2A:
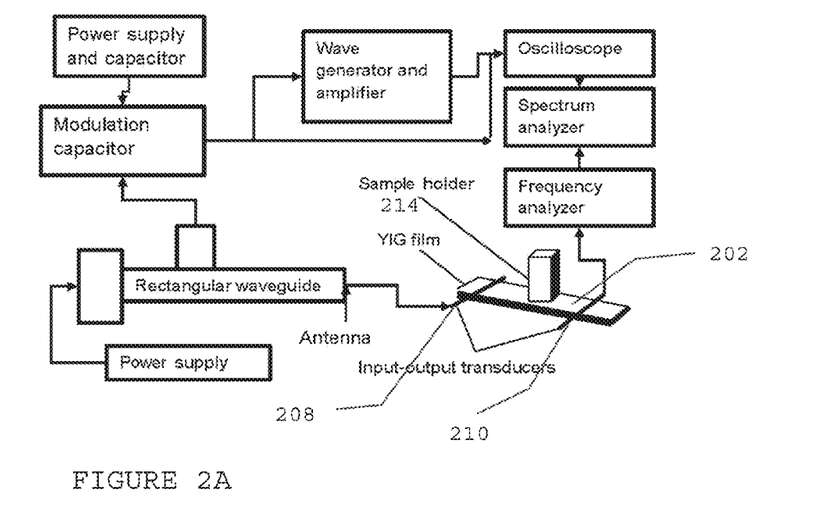
FIG. 2A shows a block diagram of the instrumentation configuration of FIG. 1 and details of physical and spacial relations of the components of the present invention.
Figure 2B:
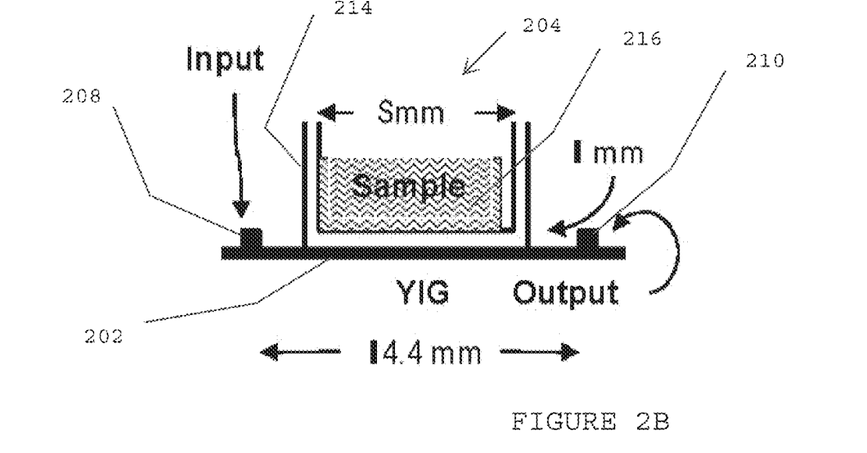
FIGS. 2B-2D illustrate in elevation and plan views respectively the components of an instrument with which the illustrative embodiments may be implemented.
Figure 2C:
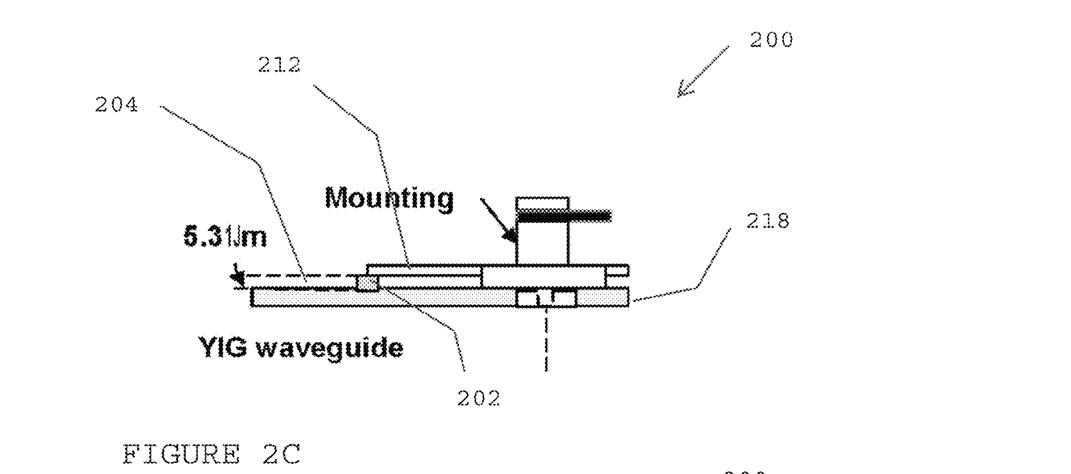
Figure 2D:
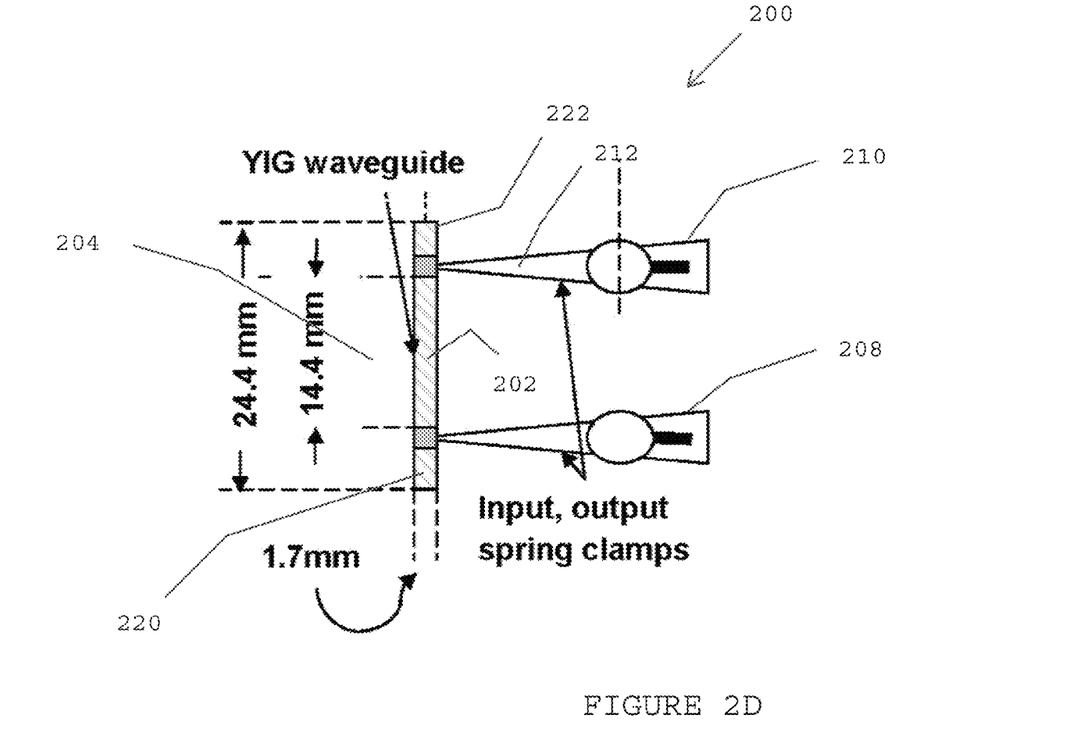

Below 100 mW operating power level for wave generator 106, a sub-optimal, linear energy response occurs in soliton electromagnetic waves 130. Above 450 mW, that energy response becomes saturated. Between 100 mW and 450 mW, the desired non-linear energy response for soliton waves such as wave 130 occurs. Accordingly, In either embodiment discussed above, wave generator 106 preferably operates to deliver non-linear soliton electromagnetic waves 130 to YIG film 202 at a power level of between 100 milliwatts (mW) and 450 mW. More preferably, wave generator operates at a power level of approximately 140 mW. At such power levels, energy response appears optimal.

Figure 3A:
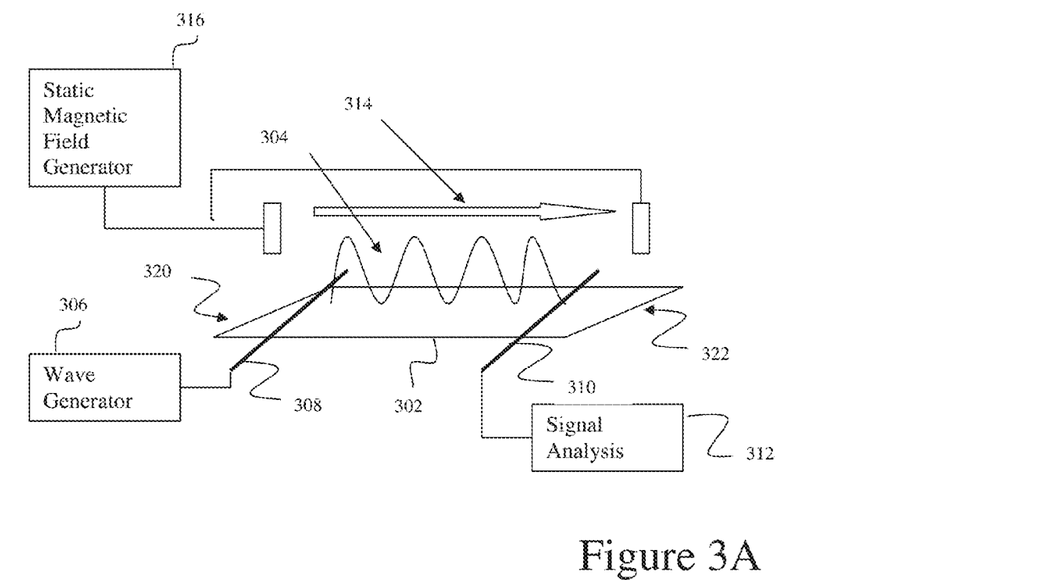
FIG. 3A is a block diagram of profiling assembly within a static magnetic field in which the illustrative embodiments may be implemented.

Referring now also to FIG. 3A, an illustrative embodiment of a magnetic field environment representing a probe system allowing magnetic resonance is depicted comprising waveguide film 302, sampling area 304, wave generator 306, excitation transducer 308, detection transducer 310, signal analysis module 312, magnetic field 314, and static magnetic field generator 316. Waveguide film 302 has input end 320 and output end 322. Waveguide film 302 is similar in structure and function to waveguide film 102 shown in FIG. 1. Sampling area 304 is similar in structure and function to sampling area 104 shown in FIG. 1. Wave generator 106 is similar in structure and function to wave generator 106 shown in FIG. 1. Excitation transducer 308 is similar in structure and function to excitation transducer 108 shown in FIG. 1. Detection transducer 310 is similar in structure and function to detection transducer 110 shown in FIG. 1. Magnetic field is similar in structure and function to magnetic field 122 shown in FIG. 1.

In a particular embodiment, magnetic field 314 is produced by static magnetic field generator 316 created by electromagnetic field coils. The strength of the magnetic field depends on the desired measurement, pole orientation, and the gyromagnetic ratio of a medium in sample area 304 and the desired resonance. For example, a YIG waveguide with a gyromagnetic ration of 2.8 GHz will require a magnetic field near 1000 Oe and with an input microwave pulse of 3.5 GHz while a microwave pulse of 4.8 GHz will require a higher magnetic field near about 1200 to about 1400 Oe.

Figure 3B:
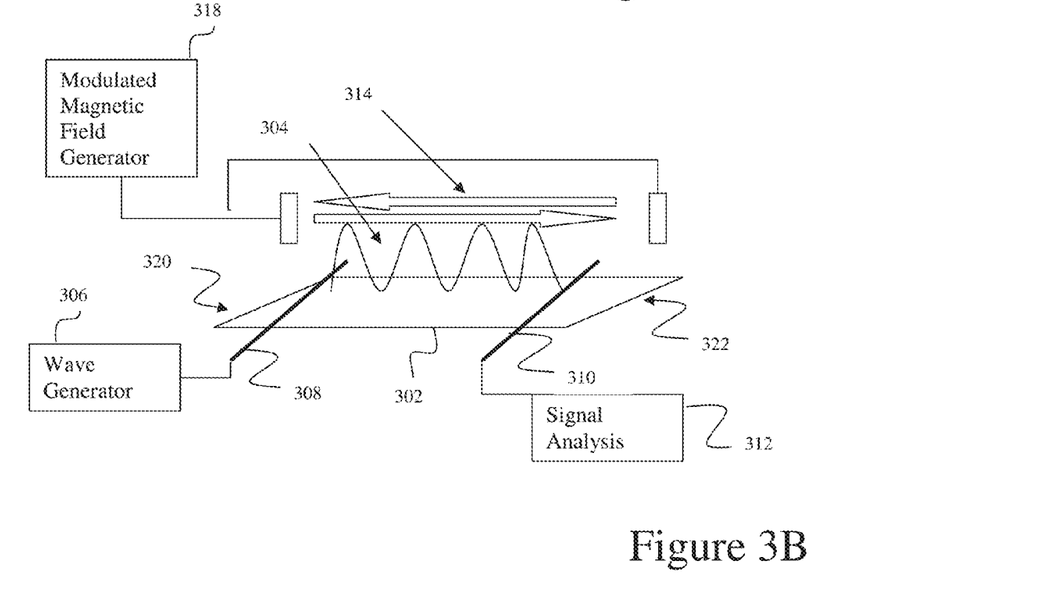
FIG. 3B is a block diagram of profiling assembly within a modulated magnetic field in which the illustrative embodiments may be implemented.

In a particular embodiment, shown in FIG. 3B, magnetic field 314 is created by modulated magnetic field generator 318 which modulates magnetic field 314 to produce a modulated magnetic resonance. A modulated magnetic resonance allows recovery of information relating to medium profile, including but not limited to charge centers, dielectric properties, plasmonic characteristics, through frequency response, and phase character. The rate of modulation depends on the medium being sampled. Waveguide film 302, sampling area 304, wave generator 306, excitation transducer 308, detection transducer 310, and signal analysis module 312 shown in FIG. 3B are the same as or similar to waveguide film 302, sampling area 304, wave generator 306, excitation transducer 308, detection transducer 310, and signal analysis module 312 shown in FIG. 3A.

EXAMPLE 1

To demonstrate consistency between sampling intervals, a test was conducted on a test sample of 0.40 milliliters (mL) of pure methanol. A YIG film 202 of 5.3 microns was developed based on a liquid phase epitaxy growth at 910 degrees Celcius. Microwave input pulse 104, 304 of 3.52 gHz and having an output pulse amplitude of 3.45, at an impulse power input of 140 mW, was directed at the sample. Static magnetic field 122, 304 of 1000 Oe+/−15 Oe was imposed.

Twelve data collection periods of two minutes each over two days were collected at a sampling rate was 8000 collection sequences per second, half on one day and half on the other to mitigate temporal environmental variables. Output data signals were processed using Fourier transform analysis.

Figure 4:
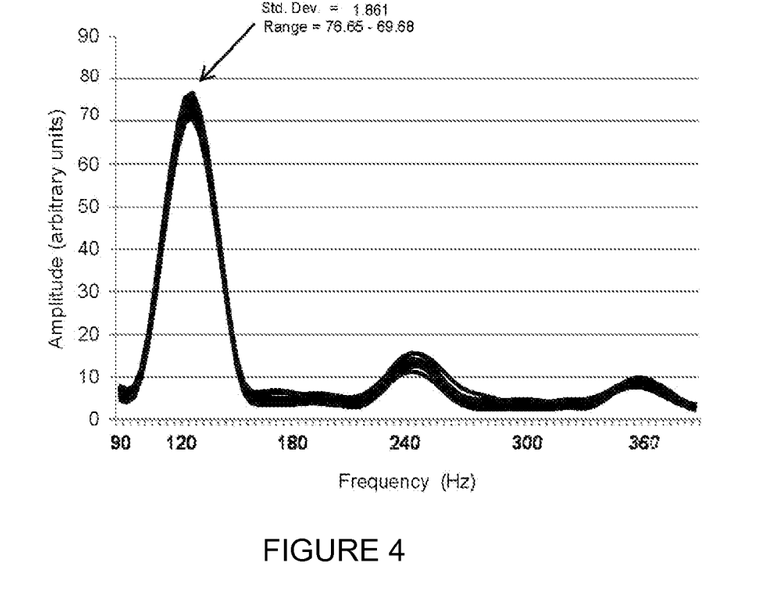
FIG. 4 shows a graph of a Fourier transform of output signals from the present invention, including multiple traces from testing of a particular sample medium.

FIG. 4 shows the Fourier spectrum observed. All traces appear substantially superimposed and exhibiting a classic Fourier transform peaking at a parent impulse frequency of 120 Hz, with minor daughter peaks at 240 Hz and 360 Hz. The amplitude range of the parent pulse falls consistently between 70 and 77 amplitude units (arbitrary units), with a standard deviation of 1.861 units. This example demonstrates consistency and accuracy of the testing instrumentation and methodology.

EXAMPLE 2

To determine standards for various sample materials, the foregoing testing procedure and equipment was applied to a variety of samples. The solvents selected for scanning included analytically pure grade water, methanol, toluene, acetone, acetonitrile, and n-propanol. Output signals were processed using methods previously described for Example 1. As a method for further signal to noise enhancement, output signals from each solvent were processed using Fourier transform and smoothing. Frequency domains were enhanced. This method indicated a strong peak at 120 Hz for all solvents with other changes seen at higher frequencies. The peak at higher frequency peak at 595 Hz was also selected for comparisons. The peak seen at 120 Hz demonstrated high amplitude and narrow peak width which is typical with soliton wave character. The smaller peaks were assumed to be daughter peaks initiated by the main peak at 120 Hz. It is important to also note that a frequency at 120 Hz also showed the greatest static field impact when field strengths were compared earlier within instrument development.

Figure 5:
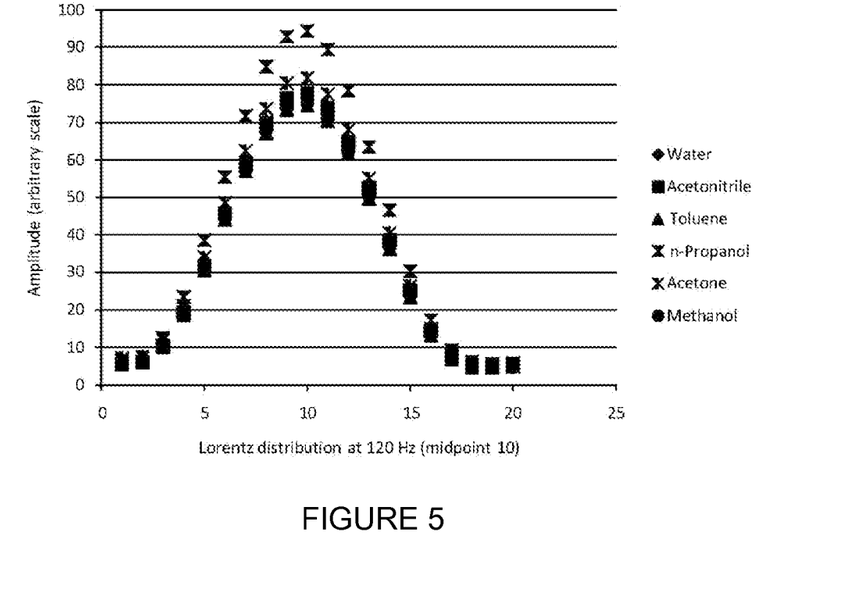
FIG. 5 illustrates a Lorentz distribution of multiple tests of multiple sample media using the present invention.

FIG. 5 shows the Lorentz distribution of the results at the 120 Hz parent impulse frequency. The daughter peaks were omitted. FIG. 5 clearly demonstrates that the apparatus and method of the present invention produced different signal curves characteristic of the different sample materials.

EXAMPLE 3

The output signals from Example 2 were further refined in an effort to mitigate potential attenuation effects by the glass cuvette. The output pulse from an empty glass cuvette was multiplied by the output pulse of a solvent to highlight common peak areas. In each case the resulting output was processed using signal-to-noise enhancement methods previously described and then Fourier transformed. Common peaks at 117 Hz, 180 Hz, 240 Hz (parent peak), 312 Hz, 360 Hz and 472 Hz. In this manner, frequency domains were enhanced and common peak amplitudes increased. Each sample exhibited a unique peak profile. The analytical process was rapid and required very limited pre-analysis sample processing.

Figure 6:
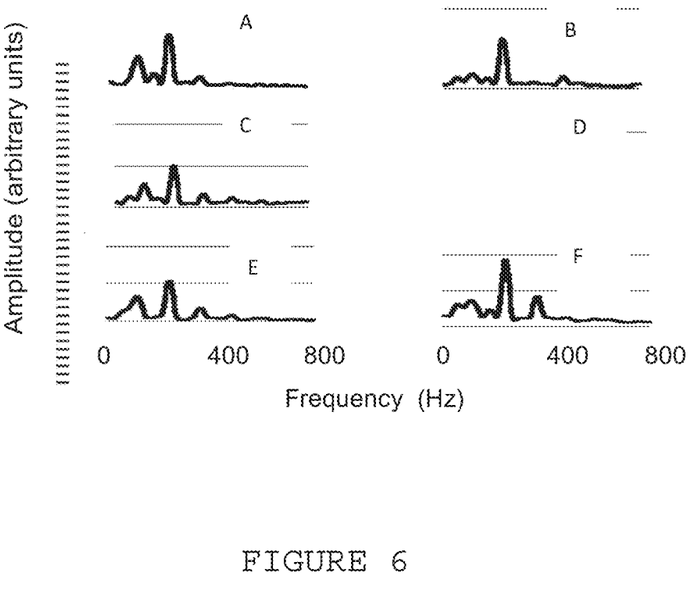
FIG. 6 illustrates Fourier transforms similar to FIG. 4 for the multiple sample media of FIG. 5.

A comparison of six solvents using like experimental procedures, input pulse and static magnetic field is given in FIG. 6. Resulting dissimilar spectra appeared for acetone (A), water (B), methanol (C), toluene (D), acetonitrile (E) and n-propanol (F). The analytical process shifted the parent pulse to 240 Hz instead of the 120 Hz of FIG. 4. The dissimilar spectra seen in each case demonstrate that this analytical technique enhances the ability to detect specific liquid material electric and magnetic properties.

Those having ordinary skill in the art will further appreciate that the various illustrative logical blocks, structures, configurations, modules, and steps described in connection with the embodiments disclosed herein may be implemented in varying ways. Various illustrative structures, components, blocks, configurations, modules, and steps have been described above generally in terms of their functionality. Skilled artisans may implement the described functionality in varying ways for each particular application, but such implementation decisions should not be interpreted as causing a departure from the scope of the present disclosure.

I claim:

1. A material charge center detector for non-invasive analysis and identification of physical media using electromagnetic waves comprising:
a waveguide having
a longitudinal axis extending between a waveguide input end and a waveguide output end;

a physical conductive structure disposed between the waveguide input end and the waveguide output end, the physical conductive structure being
coupled at the waveguide input end to an excitation transducer by a first contact probe; and
coupled at the waveguide output end to a detection transducer by a second contact probe; and
a sample testing area disposed along the longitudinal axis between the first contact probe and the second contact probe and adjacent the physical conductive structure, the sample testing area adapted to receive the physical media;
magnetic field generating means for generating a magnetic field within the waveguide;
an electromagnetic wave pulse generator coupled to the excitation transducer; and
signal analysis means coupled to the detection transducer for analyzing the electromagnetic wave pulses after they have passed through the waveguide and the physical media.

2. The material charge center detector of claim 1 wherein the physical conductive structure comprises
a rectangular conductor having a longitudinal length between 20 millimeters and 30 millimeters.

3. The material charge center detector of claim 1 wherein the physical conductive structure comprises
a rectangular conductor having a width transverse the longitudinal axis of between 1.0 millimeters and 1.5 millimeters.

4. The material charge center detector of claim 1 wherein the physical conductive structure comprises
a rectangular conductor having a thickness transverse the longitudinal axis of between 5.0-7.2 microns.

5. The material charge center detector of claim 1 wherein the physical conductive structure comprises
a rectangular conductor having
a longitudinal length between 20 millimeters and 30 millimeters;
a width transverse the longitudinal axis of between 1.0 millimeters and 1.5 millimeters; and
a thickness transverse the longitudinal axis and normal to the width and length of between 5.0-7.2 microns.

6. The material charge center detector of claim 1 wherein the waveguide is fabricated from a material selected from one of
a yttrium iron garnet (YIG),
a yttrium-aluminum garnet (YAG), and
a yttrium iron boron garnet (YIBG) waveguide.

7. The material charge center detector of claim 1 wherein the electromagnetic wave pulse generator generates a non-linear soliton wave pulse.

8. The material charge center detector of claim 7 wherein the electromagnetic wave pulse generator is a klystron microwave generator.

9. The material charge center detector of claim 1 wherein the magnetic field generating means comprises
a fixed magnet generating a static magnetic field substantially parallel to the longitudinal axis of the waveguide.

10. The material charge center detector of claim 1 wherein the magnetic field generating means comprises
a variable electromagnetic field coil generating a modulated magnetic field.

11. The material charge center detector of claim 1 and further comprising
a reference wave generator coupled between said electromagnetic wave pulse generator and said signal analysis means for transmitting a reference signal to said signal analysis means to contrast said reference signal to said electromagnetic wave pulse received by said detection transducer.

12. The material charge center detector of claim 1 wherein the signal analysis means comprises
a frequency analyzer; and
a spectrum analyzer.

13. The material charge center detector of claim 12 wherein the spectrum analyzer comprises
spectrum analyzing software running on a personal computer, said spectrum analyzing software receiving signals from the detection transducer and contrasting said signals to a known spectrum of materials for identification of said physical media.

14. An improved method of non-invasive analysis and identification of materials, the improved method comprising
providing a material charge center detector having
a waveguide having
a longitudinal axis extending between a waveguide input end and a waveguide output end;
a physical conductive structure disposed between the waveguide input end and the waveguide output end, the physical conductive structure being
coupled at the waveguide input end to an excitation transducer by a first contact probe; and
coupled at the waveguide output end to a detection transducer by a second contact probe; and
a sample testing area disposed along the longitudinal axis between the first contact probe and the second contact probe and adjacent the physical conductive structure, the sample testing area adapted to receive the physical media;
magnetic field generating means for generating a magnetic field within the waveguide;
an electromagnetic wave pulse generator coupled to the excitation transducer; and
signal analysis means coupled to the detection transducer for analyzing the electromagnetic wave pulses after they have passed through the waveguide;
providing a material sample contained within a sample vessel; then
placing the material sample and the sample vessel into the medium testing region; then
operating the electromagnetic pulse generator to generate a plurality of electromagnetic wave pulses directed through said excitation transducer toward the detection transducer and across the material sample within the medium testing region; then
detecting the plurality of electromagnetic wave pulses received from the detection transducer and passing the plurality of electromagnetic wave pulses to the signal analysis means; and
analyzing the plurality of electromagnetic wave pulses to identify the material sample within the sample vessel.

15. The improved method of claim 14 and further comprising
providing a reference wave generator coupled between the electromagnetic wave pulse generator and the signal analysis means; and
simultaneously with the operating step
creating a plurality of reference waves corresponding to the plurality of electromagnetic wave pulses; and
passing said plurality of reference waves to said signal analysis means; and contrasting said plurality of reference waves to said electromagnetic wave pulses detected by said detection transducer.

\* \* \* \* \*